United States Patent [19]

Friedman et al.

[11] Patent Number: 4,795,645

[45] Date of Patent: Jan. 3, 1989

[54] SUSTAINED RELEASE TABLETS OF THEOPHYLLINE

[75] Inventors: Michael Friedman; Meir Bialer, both of Jerusalem; Hussein Ziad, Galil Tahton, all of Israel

[73] Assignee: Yissum Research and Development, Israel

[21] Appl. No.: 938,265

[22] Filed: Nov. 25, 1986

[30] Foreign Application Priority Data

Nov. 3, 1986 [IL] Israel ........................................ 78017

[51] Int. Cl.[4] ........................... A61K 9/22; A61K 9/30
[52] U.S. Cl. ..................................... 424/468; 424/474; 424/475; 424/499
[58] Field of Search ............... 514/826, 21, 776; 424/499, 475, 474, 468

[56] References Cited

U.S. PATENT DOCUMENTS

| | | | |
|---|---|---|---|
| 3,109,775 | 11/1963 | Shepard | 167/82 |
| 3,922,379 | 11/1975 | Farhadieh | 427/3 |
| 4,002,756 | 1/1977 | Higuchi et al. | 514/826 X |
| 4,147,167 | 4/1979 | Yapel, Jr. | 424/499 |
| 4,223,031 | 9/1980 | Covington et al. | 514/826 X |
| 4,261,970 | 4/1981 | Ogawa et al. | 514/826 X |
| 4,465,660 | 8/1984 | David et al. | 424/468 X |
| 4,695,591 | 9/1987 | Hanna et al. | 424/499 X |
| 4,710,384 | 12/1987 | Rotman | 424/468 X |

FOREIGN PATENT DOCUMENTS

| | | |
|---|---|---|
| 0134290 | 3/1985 | European Pat. Off. |
| 3104815 | 1/1982 | Fed. Rep. of Germany |
| 57-106610 | 7/1982 | Japan ........................ 424/499 |

*Primary Examiner*—Thurman K. Page
*Attorney, Agent, or Firm*—Berman, Aisenberg & Platt

[57] ABSTRACT

The present invention relates to a sustained release tablet comprising an admixture of theophylline and denaturated egg-albumin. The invention relates also to a process for the preparation of said tablet and to a method for administering same to people suffering from asthma.

13 Claims, No Drawings

SUSTAINED RELEASE TABLETS OF THEOPHYLLINE

The present invention relates to sustained release tablets of theophylline for the treatment of asthma.

Theophylline relieves and/or prevents symptoms of asthma by relaxing bronchial smooth muscles. It is rapidly, consistently and completely absorbed from oral solutions and plain uncoated tablets. Absorption may be delayed, slowed or incompleted by the administration of specific formulations which decrease the rate of dissolution in the gut. Formulations having a slow but reliable absorption have a therapeutic advantage, particularly for children in whom elimination is rapid and fluctuations in serum concentrations between doses are excessive. Slow release formulations allow longer, better dosing intervals with more stable blood levels.

There are known several sustained release formulations comprising theophylline. From French Specification No. 1.443.063 there is a known coated tablet comprising theophylline and noscopine. From U.S. Specification No. 4.415.547 there is known a sustained release tablet consisting of an encapsulated drug pellet comprising as active material theophylline. From European Specification No. 109.320, Belgian Specification No. 899.293 and from Japanese Specification No. 57.171.918 there are known sustained release matrix tablets comprising theophylline as active material. Said tablets require the use of synthetic polymers which are quite expensive.

From PCT Application No. WO 83 00284 there is known a sustained release composition which is being distributed under the name Theo-Dur. In said composition theophylline is coated on sugar beads using poly(vinylpyrrolidone) as adhesive and the obtained micropellets are coated with a mixture of cellulose ethers to give the desired product. The dissolution achieved in this composition is quite satisfactory, but the manufacture of said composition is rather complicated and requires the use of rather expensive materials.

All the above known forms are not entirely satisfactory as either their manufacture is complicated and expensive or their sustained release is not easy to control.

It has thus been desirable to find a suitable formulation for a sustained release tablet comprising theophylline, which should be easy and cheap to manufacture and wherein the sustained release is easily controlled.

From DOS No. 3.104.815 there is known a very general method for the preparation of sustained release formulations comprising one or more physiologically active substances and one or more proteins. The protein is denaturated by a physical and/or chemical treatment and the denaturated protein serves, in case that it is admixed with a solid compound, as a matrix encapsulating said active compound.

Many physiologically active substances are mentioned in said specification but not theophylline. Moreover, the method described in the examples which comprises mere admixing of powders, direct preparation of pellets thereafter is not suitable in the preparation of tablets according to the present invention. The process for the manufacture of said tablets requires first the preparation of granulates of specific size which enables the free flow thereof. The tablets can be prepared only from said granulates.

It could therefore not have been foreseen that a formulation comprising theophylline and denatured egg-albumin would give a sustained release tablet having the desired quality.

The present invention thus consists in a sustained release tablet comprising an admixture of theophylline and denatured egg-albumin.

The tablets according to the present invention preferably comprise theophylline and egg-albumin in a ratio of 0.1–10:1.

Egg-albumin is commercially available. It is water soluble at ambient temperatures. When heated over 60° C. irreversible denaturation occurs resulting in insolubility in water.

Denaturation of native egg-albumin may be obtained besides by heating, by cross-linking or by an interaction with suitable denaturation agents, such as ethanol, acids, polyvalent cations and many other chemicals.

The present invention consists also in a process for the preparation of the tablet according to the present invention in which theophylline and dried egg-albumin are admixed, the mixture obtained is wetted and dried, the granulates obtained are thereafter converted into a tablet by methods known per se, and the tablets obtained are heated to at least 60° C.

The tableting is suitably performed with a lubricant, e.g. magnesium stearate. The tablet may optionally be coated, in order to obtain suitable form and/or taste, with a suitable coating agent.

The present invention is not restricted to heating for the denaturation, and any other suitable denaturation method may be utilised.

The present invention will now be illustrated with reference to the following examples without being restricted to them.

The tablets described in Examples 1 to 4 were prepared as follows:

Anhydrous theophylline and dried egg-albumin were admixed and granulated by wetting the mixture with water. The granulates obtained were heated in an oven to about 50° C. and then passed through an adequate sieve (mesh size 1.00 mm; wire diameter 0.63 mm; mesh/$cm^2$ 15) Magnesium stearate was then admixed with the granulates. The mixture obtained was passed to a tabletting machine, The obtained tablets were then passed on to an oven and heated there to 130° C.±5° for two hours and then cooled. The tablets were then coated with Opadry Y-1-7000, a composition manufactured by Colorcon, U.K.

EXAMPLE 1

The tablet comprised:

| | |
|---|---|
| Anhydrous theophylline | 100 mg |
| Dried egg-albumin | ca. 20 mg |
| Magnesium stearate | ca. 0.3 mg |
| White Opady Y-1-7000 | q.s. (2–4%) |
| Diameter of the tablet | 7 ± 0.01 mm |
| Thickness of the tablet | 3.1 ± 0.2 mm |
| Hardness of core | not less than 3 kg |
| Weight of the tablet | ca. 120 mg |

(The weight of the tablet was determined by the analysis of the tablet in order that it should comprise the above amount of theophylline.)

EXAMPLE 2

The tablet comprised:

| Anhydrous theophylline | 200 mg |
| Dried egg-albumin | ca. 40 mg |
| Magnesium stearate | ca. 0.6 mg |
| White Opady Y-1-7000 | q.s. (2–4%) |
| Diameter of the tablet | 9.5 ± 0.2 mm |
| Thickness of the tablet | 3.5 ± 0.3 mm |
| Hardness of core | not less than 4 kg |
| Weight of the tablet | ca. 240 mg |

EXAMPLE 3

The tablet comprised

| Anhydrous theophylline | 300 mg |
| Dried egg-albumin | ca. 60 mg |
| Magnesium stearate | ca. 0.9 mg |
| White Opadry Y-1-7000 | q.s. (2–4%) |
| Diameter of the tablet | 11.0 ± 0.3 mm |
| Thickness of the tablet | 3.8 ± 0.4 mm |
| Hardness of the core | not less than 5 kg |
| Weight of the tablet | ca. 360 mg. |

EXAMPLE 4

The tablet comprised:

| Anhydrous theophylline | 300 mg |
| Dried egg-albumin | ca. 90 mg |
| Magnesium stearate | ca. 0.9 mg |
| White Opadry Y-1-7000 | q.s. (2–4%) |
| Diameter of the tablet | 11.0 ± 0.3 mm |
| Thickness of the tablet | 3.8 ± 0.4 mm |
| Hardness of the core | not less than 5 kg |
| Weight of the tablet | ca. 390 mg |

EXAMPLE 5

The release rate of theophylline from the tablets obtained in Examples 1 to 4 was measured by the following procedure.

Equipment and Solutions

Standard USP dissolution apparatus was used in all of the dissolution rate measurements.

Solutions

1. Gastric fluid USP XX (pH 1.5 with pepsin)
2. Intestinal fluid USP XX (pH 6.9 with pancreatine)
3. Standard theophylline solutions.

Procedure

The tested theophyllline tablets were placed in the dissolution beaker container simulated gastric fluid. At suitable intervals samples of the dissolution solutions were withdrawn, centrifuged and the amounts of theophylline released were determined spectrophotometrically at 272 nm. After 2 hours the dissolving medium was totally replaced by the artificial intestinal fluid. The sampling and the theophylline release determination was continued up to 12 hours.

The results of said experiments are shown in Table 1.

TABLE 1

| Time (Hours) | Amount Released % for each Example | | | |
|---|---|---|---|---|
| | 1 | 2 | 3 | 4 |
| 0.5 | 12.1 | 13.8 | 11.0 | 12.8 |
| 1.0 | 17.9 | 21.7 | 18.8 | 19.9 |
| 2.0 | 27.7 | 30.2 | 32.5 | 27.4 |
| 3.0 | 32.5 | 35.2 | 39.8 | 32.2 |
| 4.0 | 39.7 | 42.1 | 45.6 | 38.4 |
| 5.0 | 43.3 | 47.6 | 51.3 | 42.1 |
| 6.0 | 50.5 | 54.2 | 56.8 | 45.0 |
| 7.0 | 53.4 | 58.1 | 62.5 | 47.9 |
| 8.0 | 59.8 | 61.4 | 67.3 | 50.6 |
| 10.0 | 69.8 | 72.3 | 78.4 | 64.2 |
| 12.0 | 78.2 | 80.0 | 87.2 | 72.4 |

EXAMPLE 6

In a similar manner to that described for the preparation of tablets in Examples 1 to 4 several tablets were prepared. No coating procedure was performed. Each tablet contained 300 mg of theophylline but the amount of dried egg-albumin was varied. There were prepared tablets comprising:

| 75 mg dried egg-albumin |
| 150 mg dried egg-albumin |
| 300 mg dried egg-albumin |
| 600 mg dried egg-albumin |
| 900 mg dried egg-albumin |

The release rate of theophylline from the tablets obtained was measured in the same manner as described in Example 5.

The results of said experiments ae given in Table 2.

TABLE 2

| Tablet Content | | | Amount of theophylline released (%) | | | | | | | | | |
|---|---|---|---|---|---|---|---|---|---|---|---|---|
| Theophylline (mg) | Egg albumin (mg) | Time (hr) | 0.5 | 1 | 1.5 | 2 | 3 | 4 | 5 | 6 | 8 | 12 |
| 300 | 75 | | 12.5 | 17.90 | 22.98 | 26.64 | 32.00 | 37.52 | 45.71 | 50.00 | 58.200 | 72.500 |
| 300 | 150 | | 9.78 | 15.02 | 17.70 | 20.37 | 31.98 | 37.69 | 44.52 | 48.90 | 56.29 | 70.25 |
| 300 | 300 | | 5.94 | 9.28 | 11.96 | 14.23 | 16.73 | 19.73 | 22.85 | 25.68 | 33.92 | 45.00 |
| 300 | 600 | | 4.23 | 6.21 | 8.09 | 9.67 | 14.28 | 16.17 | 16.56 | 18.81 | 24.34 | 33.23 |
| 300 | 900 | | 3.14 | 5.12 | 6.64 | 8.20 | 13.70 | 15.29 | 16.55 | 17.72 | 19.94 | 23.80 |

EXAMPLE 7

The pharmacokinetic performance of tablets having the formulation and properties given in Example 3 (hereinafter called Theotrim) was measured. The experiments were performed as follows:

Material and Methods

Five male volunteers aged between 24 and 32 years, weighing 65–82 kg were selected on the basis of negative medical history, physical examination, normal routine chemical blood analysis and morphology and urine analysis. Each patient received at a separate time one tablet of Theotrim.

Each tablet was administered at 8.00 a.m. after an overnight fast. Food was withheld for 5 hours after the administration of each theophylline formulation. Tea, coffee, coke and other caffeinated beverages and food were not allowed from two days before, until the end of each study.

Various blood samples (10 ml) were taken via an indwelling catheter from the forearm vein at 0.5, 1, 1.5, 2, 3, 4, 5, 6, 8, 10, 12, 14, 16, 24, 30, 38 and 48 hours after the oral administration. The plasma was immediately separated by centrifugation at 7000 rpm for 15 min. and stored at $-20°$ C. Before assaying, the plasma was allowed to reach room temperature, vortexed, centrifuged and the residual clot removed. Plasma theophylline levels were determined at HPLC at a UV wavelength of $\lambda=275$ nm. The assay procedure was a modification of a method published by J. J. Orcid et al., Clin. Chem. 27, 2071-2072 (1981).

Each sample was assayed in triplicate with an eight point calibration curve (containing plasma from each patient before the administration of the theophylline formulation, t=0), spiked with known amounts of theophylline.

The linear terminal slope ($\beta$) of the log Cb Theophylline serum concentration) vs. t (time) plot was calculated by the method of least squares. The half-life of theophylline (t ½ $\beta$) was calculated from the quotient.

$$\frac{0.69}{\text{terminal slope}}$$

The AUC (area under the Cb. vs. t curve) was calculated using the trapezoidal rule, with extrapolation to infinity by dividing the last experimental point by the linear terminal slope. The peak serum concentration of theophylline ($Cb_{max}$) and the time to reach $Cb_{max}(t_{max})$ were reported.

A statistical analysis was conducted for measuring various pharmacokinetic parameters, such as: t ½ $\beta$, AUC, and $Cb_{max}$.

Results

Individual and mean plasma concentrations obtained after the administration of the theophylline formulation are presented in Table 3. The plasma concentrations are expressed therein in mg/L. Table 4 summarizes the various pharmacokinetic parameters obtained after the administration of the theophylline formulation. The theophylline half-life obtained was similar to that obtained by L. Hendeles et al., Am. J. Hosp. Pharm. 34, 525-527 (1977).

The various pharmacokinetic parameters presented in Table 4 were calculated individually for each patient. The mean data presented in Table 4 are the average of the various individual pharmacokinetic parameters.

The tables mentioned above are given hereinafter.

TABLE 3

| Subject Time (hr.) | H.D. | R.A. | K.I. | H.H. | S.D. | Mean ± S.D. |
|---|---|---|---|---|---|---|
| 0.5 | 0.9 | 0.5 | 1.5 | 0.9 | 0.9 | 0.9 ± 0.4 |
| 1.0 | 1.1 | 1.1 | 1.9 | 1.3 | 1.9 | 1.5 ± 1.4 |
| 1.5 | 1.6 | 2.2 | 2.1 | 1.9 | 2.1 | 2.0 ± 0.2 |
| 2.0 | 2.0 | 2.5 | 2.4 | 2.6 | 2.3 | 2.4 ± 0.2 |
| 3.0 | 2.6 | 2.9 | 2.6 | 3.3 | 2.5 | 2.8 ± 0.3 |
| 4.0 | 3.7 | 5.4 | 3.7 | 3.7 | 2.7 | 3.7 ± 1.0 |
| 5.0 | 4.1 | 6.1 | 3.4 | 3.9 | 2.8 | 4.1 ± 1.2 |
| 6.0 | 4.3 | 6.6 | 3.8 | 5.3 | 2.9 | 4.6 ± 1.4 |
| 8.0 | 4.4 | 6.8 | 4.9 | 5.5 | 2.4 | 4.7 ± 1.6 |
| 10.0 | 3.4 | 5.1 | 5.0 | 5.5 | 2.1 | 4.2 ± 1.4. |
| 12.0 | 3.0 | 4.0 | 4.4 | 4.8 | 1.8 | 3.6 ± 1.2 |
| 14.0 | 2.6 | 3.6 | 4.0 | 4.1 | 1.3 | 3.2 ± 1.2 |
| 16.0 | 2.0 | 2.6 | 3.5 | 3.4 | 1.2 | 2.9 ± 1.6 |
| 24.0 | 1.4 | 1.2 | 2.2 | 2.4 | 0.7 | 1.6 ± 0.7 |
| 30.0 | 1.1 | 0.6 | 1.2 | 2.2 | 0.3 | 1.1 ± 0.7 |

TABLE 3-continued

| Subject Time (hr.) | H.D. | R.A. | K.I. | H.H. | S.D. | Mean ± S.D. |
|---|---|---|---|---|---|---|
| 38.0 | 0.8 | 0.3 | 0.7 | 1.4 | 0.2 | 0.7 ± 0.5 |
| 48.0 | 0.5 | 0.1 | 0.5 | 0.8 | 0.1 | 0.4 ± 0.3 |

TABLE 4

| Subject Pharmacok. Parameters | H.D. | R.A. | K.I. | H.H. | S.D. | Mean ± SD |
|---|---|---|---|---|---|---|
| $\beta(hr^{-1})$ | 0.51 | 0.102 | 0.738 | 0.047 | 0.083 | 0.0714 ± 0.022 |
| t½ (hr) | 13.64 | 6.82 | 9.37 | 14.78 | 8.35 | 10.59 ± 3.45 |
| Cb max (mg/L) | 4.42 | 6.83 | 5.04 | 5.49 | 2.90 | 4.94 ± 1.44 |
| t max (hr) | 8.0 | 8 | 10 | 10 | 6 | 8.40 ± 1.67 |
| AUC (mg/hr/l) | 93 | 95 | 107 | 148 | 48 | 98.2 ± 35.76 |

Key $\beta$—Linear terminal slope
t ½ $\beta$—Terminal half-life
Cb max—Peak plasma concentration
t max—Time to reach Cb max
AUC—Area under Cb vs. t plot Conclusions From theoretical multiple dose calculations (based on the experimental data obtained in this single dose study) it seems that a daily base of 600 to 900 mg of Theotrim can maintain steady-state plasma levels of theophylline within its therapeutic window with a relatively small percentage fluctuation.

From comparative experiments performed, it was found that Theotrim and Theo-Dur are bioequivalent. However, as indicated above, the manufacture of the later is quite complicated and requires the use of rather expensive materials.

We claim:

1. A sustained release tablet comprising an admixture of theophylline and denaturated egg-albumin.

2. A tablet according to claim 1 comprising theophylline and egg-albumin in a ratio of 0.1-10:1.

3. A tablet according to claim 1 comprising a lubricant.

4. A tablet according to claim 3, wherein the lubricant is magnesium stearate.

5. A tablet according to claim 1 comprising a coating agent.

6. A process for the preparation of a tablet according to claim 1, in which theophylline and dried egg-albumin are admixed, the obtained mixture is wetted and dried, the obtained granulate is thereafter tableted and each obtained tablet is heated to at least 60° C.

7. A process according to claim 6, wherein the tablets are prepared with a lubricant.

8. A process according to claim 6 wherein an obtained tablet is coated with a coating agent.

9. A method for the treatment of asthma comprising daily administering from 600 to 900 mg of theophylline in the form of one or more tablets claimed in claim 1.

10. A method which comprises admixing egg albumin with theophylline and denaturing the egg albumin in situ.

11. A method according to claim 10 which further comprises tableting the resulting admixture of egg albumin and theophylline prior to denaturing the egg albumin.

12. A method according to claim 10 wherein the ratio of theophylline to egg albumin is from (0.1 to 10):1.

13. A process according to claim 7 wherein the lubricant is a magnesium stearate.

* * * * *